United States Patent [19]

Faddis

[11] Patent Number: 5,334,355
[45] Date of Patent: Aug. 2, 1994

[54] OZONE STERILIZATION SYSTEM SPENT STERILIZATION AGENT DESTRUCT AND AMBIENT AIR MIXING DEVICE

[75] Inventor: Chris G. Faddis, West Valley City, Utah

[73] Assignee: Cyclo3pss Medical Systems, Inc., Salt Lake City, Utah

[21] Appl. No.: 31,219

[22] Filed: Mar. 12, 1993

[51] Int. Cl.$^5$ .................. B01D 53/36; F01N 3/10; G05D 23/00
[52] U.S. Cl. .................. 422/122; 422/109; 422/174; 422/177; 422/292; 422/305; 422/30
[58] Field of Search .......... 422/109, 120, 122, 168, 422/171, 173, 177, 124, 174, 211, 181, 186.2, 186.07, 292, 305, 30

[56] References Cited

U.S. PATENT DOCUMENTS

| | | | |
|---|---|---|---|
| 3,744,249 | 7/1973 | August | 422/174 |
| 4,225,561 | 9/1980 | Torres | 422/177 |
| 4,235,846 | 11/1980 | Abthoff et al. | 422/171 |
| 4,627,924 | 12/1986 | Coste | 422/186.2 |
| 4,780,277 | 10/1988 | Tanaka et al. | 422/4 |
| 5,069,880 | 12/1991 | Karlson | 422/186.19 |
| 5,087,419 | 2/1991 | Lutz | 422/28 |
| 5,116,574 | 5/1992 | Pearson | 422/186.07 |
| 5,116,581 | 5/1992 | Cyron et al. | 422/181 |
| 5,118,471 | 6/1992 | Andersen et al. | 422/34 |
| 5,120,512 | 6/1992 | Masuda | 422/297 |
| 5,229,071 | 7/1993 | Meo, III | 422/30 |
| 5,266,275 | 11/1993 | Faddis | 422/28 |

Primary Examiner—Robert J. Warden
Assistant Examiner—T. A. Trembley
Attorney, Agent, or Firm—M. Reid Russell

[57] ABSTRACT

A spent sterilization agent destruct and ambient air mixing device for inclusion with medial instrument sterilization system that preferably utilizes humidified ozone $O_3$ as a sterilization agent or sterilizing effluent. The invention is for receiving a spent sterilization agent flow that includes humidified ozone $O_3$ and oxygen $O_2$ and provides, within the device, for exposure of that spent sterilization agent to both a catalytic converter and to an application of heat that converts ozone $O_3$ to oxygen $O_2$, thereby rendering the sterilization agent inert, and provides for mixing that inert flow with ambient air and venting to atmosphere.

5 Claims, 5 Drawing Sheets

OZONE STERILIZATION SYSTEM SPENT STERILIZATION AGENT DESTRUCT AND AMBIENT AIR MIXING DEVICE

BACKGROUND OF THE INVENTION

1. Field of the Invention

This invention relates to medical instrument sterilization systems, and in particular to sterilization systems that utilize a highly caustic material, such as Ozone (Os), as the sterilization agent, and provides for neutralization of the agent to an inert state and venting it to atmosphere.

2. Prior Art

Humidification technologies have long been employed in the field of medical instrument sterilization, and even systems utilizing ozone ($O_3$) as the sterilization agent in such systems have previously been utilized. None have, however, provided for a thorough venting of the sterilization agent from both a primary sterilization chamber and a separate containment system to a remote agent destruct chamber wherein the agent is neutralized to an inert state, with that inert agent then vented to atmosphere. Nor has any earlier system monitored interior conditions in such destruct chamber to verify a complete heat and catalytic action neutralization of the sterilization agent prior to venting of which inert agent to atmosphere. Which structure and features are provided by the present invention.

Some examples of medical equipment sterilization systems that utilize humidification technologies with humidified ozone as the sterilization agent are shown in patents to Masuda, U.S. Pat. No. 5,120,512 and to Karlson, U.S. Pat. No. 5,069,880; and a plurality of container and chamber arrangements for use in sterilization processes utilizing ozone as the effluent are shown in patents to Anderson, et al, U.S. Pat. No. 5,118,471; and to Lutz, U.S. Pat. No. 5,087,419.

Unlike the present invention, however, none of the above cited earlier systems employ a system for venting sterilization agent from a primary sterilization chamber and a secondary safety chamber that contains the primary sterilization chamber during a sterilization cycle into a destruct chamber. Nor do such systems provide for a separate sterilization agent neutralization and venting to atmosphere and for sensing conditions in which destruct chamber to verify a complete neutralization of which sterilization agent prior to venting.

A separate sterilization effluent heat destruction chamber and venting to atmosphere of the inert ozone oxygen mixture is mentioned, but not claimed, in earlier applications of the invention entitled, "Ozone Sterilization System Secondary Safety Chamber" Ser. No 07/940,034, and "Ozone Sterilization System Primary Sterilization and Transport Container" Ser. No 07/940,850.

SUMMARY OF THE INVENTION

It is a principal object of the present invention in an ozone sterilization system spent effluent destruct and ambient air mixing device to provide a destruct device for receiving a spent sterilization agent discharged from a primary medical instruments sterilization chamber and providing for a destruction of that agent by a controlled exposure to heat and a catalytic action.

Another object of the present invention is to provide a destruct and ambient air mixing device for destruction of a spent sterilization agent passed thereto by exposure to a heat source and by catalytic action taking place within a destruction chamber, and provides for sensing temperature within the chamber for closely monitoring the heat generated by which heat source to insure a complete destruction of the sterilization agent.

Another object of the present invention is to provide a destruct and ambient air mixing device that includes a catalytic converter and heat source for receiving and converting a spent sterilizing agent to an inert state for mixing with ambient air and dispersion out through a multi-ported delivery system to atmosphere.

Still another object of the present invention is to provide a destruct and ambient air mixing device for receiving a spent sterilization agent that is a mix of ozone $O_3$ and oxygen $O_2$ with water vapor, which agent, by exposure to a catalytic action and heating in the destruction chamber, is converted from ozone $O_3$ to oxygen $O_2$, is mixed with ambient air and dispersed to atmosphere.

Still another object of the present invention is to provide a destruct and ambient air mixing device for utilization in a medical instrument ozone sterilization system, the device for receiving and neutralizing a spent sterilization agent mix of ozone $O_3$ and oxygen $O_2$ with water vapor by a catalytic action and application of a controlled heat to render the agent inert for mixing with ambient air drawn into the destruction chamber and dispersion to atmosphere through a multi-ported vent system.

The invention is in a destruct and ambient air mixing device that is a component of a medical instrument sterilization system. The system sterilization agent is preferably a mix of ozone $O_3$ and $O_2$ that has been humidified and circulated through a system primary sterilization chamber for sterilizing medical instruments therein. The destruct and ambient air mixing device of the invention includes a closed destruction chamber, preferably an insulated outer body that is closed on both ends, and an inner heat conductive cylinder that is open therethrough. The outer body, on one end, connects to a T coupling to receive spent sterilization agent therethrough. The T coupling is connected to outlet lines from the sterilization system primary sterilization and secondary safety chambers and a vent line, venting the spent ozone, oxygen and water vapor mixture therethrough into the invention.

The destruct and ambient air mixing device destruction chamber inner cylinder maintains a catalytic converter that is arranged as a roll fitter in which inner cylinder that the spent sterilization agent it passed into wherein a chemical reaction takes place where the ozone $O_3$ is converted of oxygen $O_2$. Which conversion preferably takes place in the presence of heat generated by heater plates maintained to the inner cylinder. With the heat generated by which heater plates monitored by a thermostat sensor switch that commands passage and cutting off of an electrical current to which heater plates that are thereby heated to maintain a desired temperature within the inner cylinder. Which desired temperature is transferred to within the catalytic converter reliably convert all the spent sterilization agent to an inert state with all ozone $O_3$ transformed to oxygen $O_2$. The inert spent sterilization agent mixture is then mixed with a flow of ambient air draw from the surrounding atmosphere and is dispersed through a multi-ported vent system to atmosphere.

DESCRIPTION OF THE DRAWINGS

In the drawings that illustrate that which is presently regarded as the best mode for carrying out the invention.

DETAILED DESCRIPTION

Figure 1:
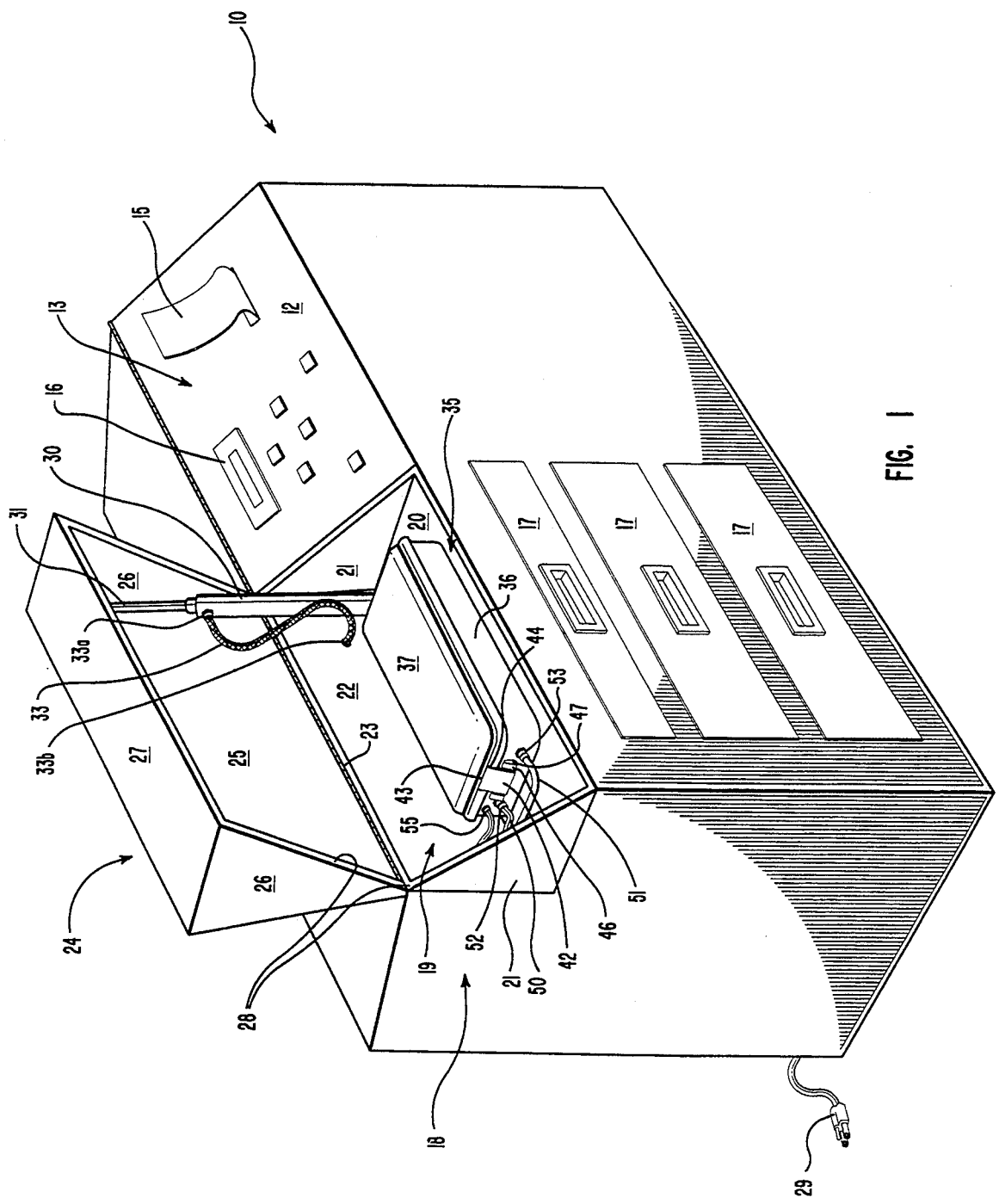
FIG. 1 is a profile perspective view of a console containing an ozone sterilization system that includes the invention in a spent sterilization agent destruct and ambient air mixing device, and showing a clam shell type lid, covering a top section of the console, in an open attitude exposing a compartment that is a secondary safety chamber for containing a primary sterilization and transport chamber wherein medical instrument sterilization takes place.

FIG. 1 shows a console 10 that contains, as shown in the block flow schematic view of FIG. 3, a medical instrument sterilization system 11, hereinafter referred to as sterilization system, that includes a sterilization system spent sterilization agent destruct and ambient air mixing device 64 of the invention, hereinafter referred to as destruct device. The sterilization system 11 utilizes ozone ($O_3$) to sterilize medical instruments that is formed from oxygen $O_2$, with the sterilization agent including a mixture of both ozone $O_3$ and oxygen $O_2$ that is humidified by introduction of a controlled volume of water vapor, as set out later herein. The destruct device 64 of the invention is preferred for use in the sterilization system 11 for neutralizing ozone $O_3$ to where it is safe for venting to atmosphere. It should, however, be understood that the destruct device of the invention could be incorporated into another sterilization system and even one utilizing a sterilization agent other than ozone $O_3$, providing that agent can be broken down to an inert state by a catalytic action, with or without heat, for neutralizing spent sterilization agent, within the scope of this disclosure.

Figure 2:
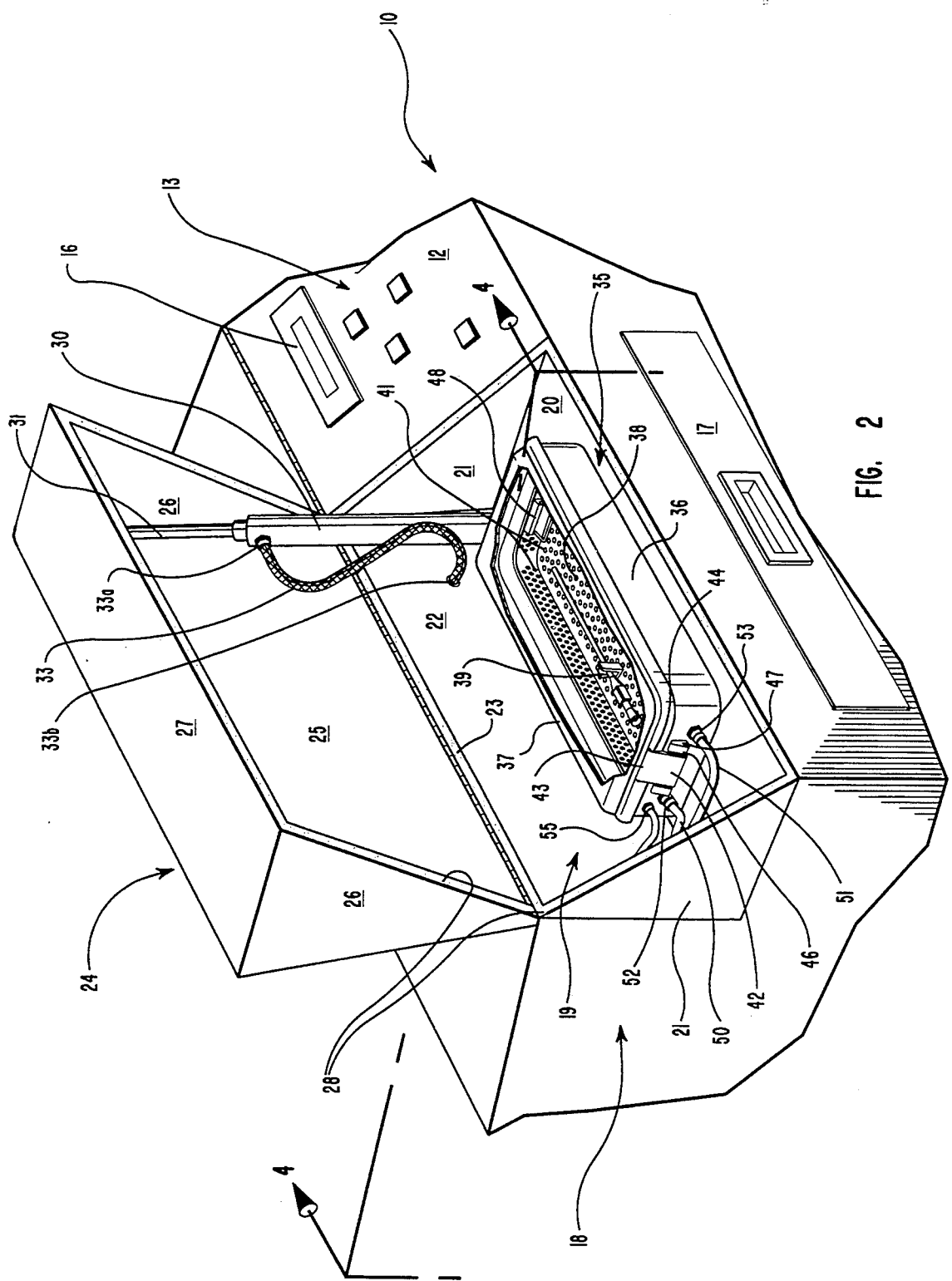
FIG. 2 is an enlarged view of a section of the console of FIG. 1, showing the clam shell type lid that includes a pneumatic piston arrangement for lifting and lowering which lid, and showing a section of the primary sterilization chamber lid broken away exposing a pan wherein medical instruments are arranged for sterilization.

In FIGS. 1 and 2, a sloping right side 12 of the console 10 is shown to include a control panel 13. The control panel 13 is shown also in the schematic of FIG. 3 as a number of buttons that connect through a programmable logic circuit (PLC) 14, that is shown also in FIG. 5. The control panel 13 buttons are for use by an operator who programs the sterilization system 11 operation. With the programmable logic circuit (PLC) 14 processing that input to operate the system components, as set out below. In which system operation a printer 15 is connected to produce an output from the programmable logic circuit 14, providing a printed record of systems operation. A display 16 is shown provided with which control panel 13 for providing a display of system readouts over time.

Figure 4:
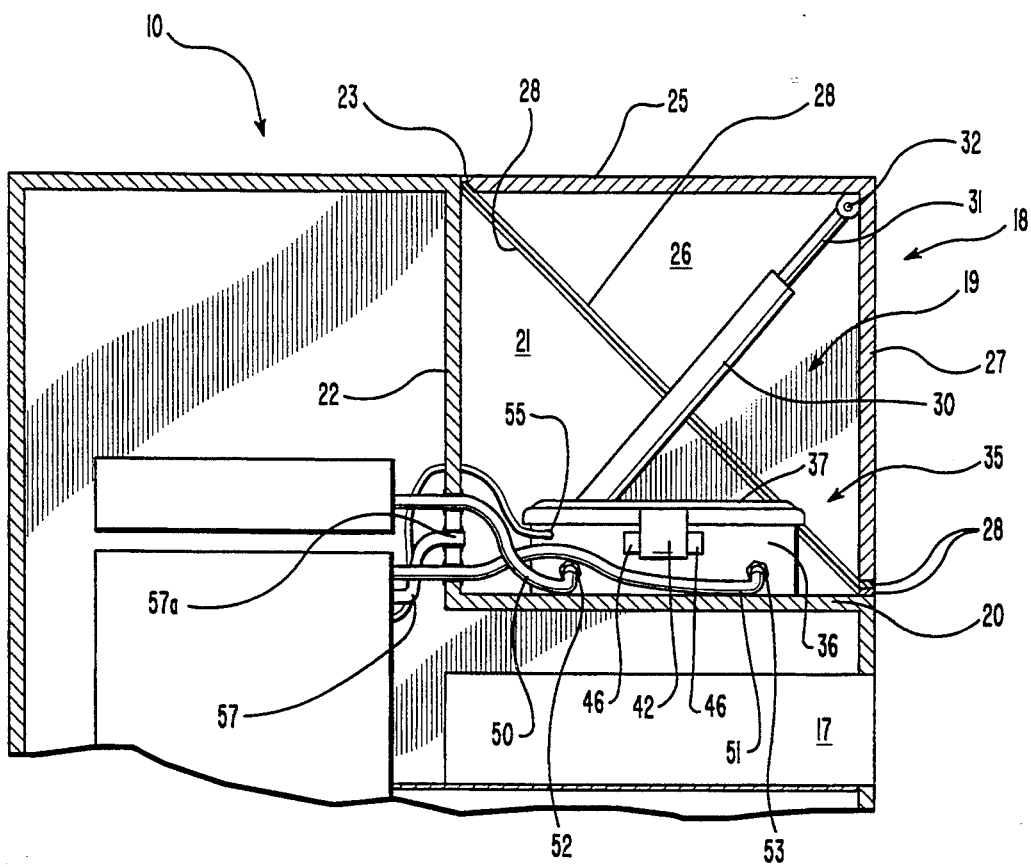
FIG. 4 is a side elevation sectional view taken along the line 4—4 of FIG. 2, only showing the clam shell type lid closed over the compartment.

As shown in FIG. 1, the left side of console 10, in a lower section thereof, includes a stack of drawers 17, for storage of system accessories, tools, and the like, and an electrical plug 29 is shown for connecting the system to a source of electricity. FIGS. 1, 2 and 4, show a secondary safety chamber 18 of the invention, hereinafter referred to as secondary chamber, formed as a rectangular console compartment 19 that is located in the top left side thereof, alongside the control panel 13. The compartment 19, with a clam shell type lid 24 fitted thereon, has a rectangular shape with identical flat bottom 20, and top 25, with right angle back and front walls 22 and 27 respectively, and side walls that are cut on the bias into sections 21 and 26, respectively. A top edge of the back wall 22 is connected through a hinge 23 to a rear edge of top 25. The clam shell type lid 24, hereinafter referred to as lid, is thereby formed by the top wall 25, side wall sections 26 and front wall 27, respectively. Lid 24 is a complement to the compartment 19 bottom portion that consists of bottom 20, side wall sections 21 and back wall 22. The lid 24 side wall sections 26 and front wall 27 edges, respectively, are flush with and engage the edges of which compartment bottom portion side wall sections 21 and back wall 22. Which compartment walls and the console are preferably formed of steel panels with the panel joints sealed. Though other suitable material could be used in their construction within the scope of this disclosure. Seals 28 are provided along the lid and compartment opposing surfaces for contacting one another when the lid 24 is closed, as shown in FIG. 4, for sealing the compartment 19 interior off from the surrounding area. Which seals 28, in practice are preferably a silicon sheet material such as a product known as Silastic, manufactured by General Electric Corporation.

The secondary chamber 18 is to be maintained in a closed sealed attitude during a sterilization cycle. To provide which locking, an actuator 30, that may to hydraulic or pneumatic, but is preferably pneumatic, is pivotally coupled at one end to the compartment 19 bottom 20 and includes a rod 31 that extends outwardly from its opposite end. The rod end within the actuator 30 is secured to a piston, not shown, and is pivotally coupled on its opposite end at 32 to the junction of the lid top 25 and front wall 27, as shown best in FIG. 4. A pressure hose 33 is shown in FIGS. 1 and 2 connected at one end 33a into the actuator 30, proximate to the end wherefrom the rod 31 extends, and is fitted through the compartment 19 back wall 22 at 33b to connect to a source of air under pressure, not shown. When the sterilization system 10 is not in operation, the compressed air in the actuator acts as a brake against rod 31 travel, affording resistance to travel by an operator lifting or lowering the lid 24, pivoting around the hinge 23. When the sterilization system 10 is in operation, air under pressure is available in the actuator 30. The rod 31 is there by urged into which actuator, pulling the lid 24 edges into close fitting contact with the compartment bottom portion edges, compressing the seal 28.

The compartment interior is thereby sealed against leakage to atmosphere so long as the sterilization cycle is in process and so long as sterilization agent or effluent presence is sensed in the secondary chamber 18 or in a primary sterilization chamber 35, as set out hereinbelow.

As shown in the drawings, the secondary chamber 18 contains a primary sterilization and transport chamber 35, hereinafter referred to as primary chamber 35. Shown best in FIGS. 1, 2 and 4, the primary chamber 35 is preferably a rectangular pan 36 for covering by a lid 37, and, as shown best in FIG. 2, contains an instrument holding tray 38, hereinafter referred to as tray. Tray 38 may include an instrument mount 39 or mounts, for holding an instrument 40 during its sterilization, or may have a flat bottom surface, within the scope of this disclosure. All of which components are preferable formed from a rigid material, such as stainless steel, that is not affected by the sterilization agent or effluent, preferably humidified ozone, that is used in the sterilization process carried on in primary chamber 35. Preferably the tray 38 has a number of holes 41 formed through its bottom and side walls for promoting circulation of a sterilizing agent in, around and through the instrument 40, thoroughly cleaning and sterilizing all of the instrument 40 surfaces and crevices.

The lid 37 is for fitting, in sealing engagement, over the pan 36 during a medical instrument sterilization cycle and during transport of the primary chamber 35 containing sterilized medical instruments to an operating room wherein the seal is broken by operating room personnel, as discussed hereinbelow. To provide this sealed engagement, the opposing lid and pan edges are formed to overlay one another, fitting closely together. Additionally, as needed, a seal is arranged between the opposing lid and pan edges for providing an air tight seal when the edges are compressed together. Which seal is formed of a material that is not reactive with ozone, such as a silicon sheet material, identified as Silastic, manufactured by General Electric Corporation, or a like material.

In practice, as set out above, a preferred sterilization agent or effluent is ozone gas that has been humidified after formation and is at or near atmospheric pressure and standard or room temperature. Accordingly, the seal in both the primary and secondary chambers 35 and 19 is not required to contain high pressures or temperatures.

To provide for compressing the lid and tray edges together, pan handles 42 are provided on opposite pan ends. Each pan handle 42 includes a hook 43, or bent over end, that is for fitting into a groove 44 formed into the center of an end section of a step that is arranged around the lid 37. Each handle 42 opposite end is for pivot coupling to the pan ends and is bent upon itself into a tube end, not shown. A pin 47 is fitted through the handle tube end, not shown, and through aligned holes or openings that are formed through a pair of piers 46 that are secured to and extend outwardly from the pan ends. So arranged, each handle 42 is free to pivot around pin 47 coupling with the pan 36 end, and is bowed outwardly across its center such that an operator can apply pressure to the bow, flexing it inwardly to where its hook end 43 will slid over the lid edge and into the groove 44. Whereafter, the operator releases pressure on the handle 42 that will then return to its original bowed state, drawing the hook end 43 into which lid edge groove 44, and pulling which lid edge into sealing engagement with the pan edge. The handles 42 pivot couplings through pins 47 that are maintained across piers 46 also provide gripping surfaces for facilitating an operator lifting the primary chamber 35 out from the secondary chamber 18 and carrying it to an operating room. For opening the primary chamber, the handles 42 are flexed inwardly against their bow, releasing the lid 37, to expose the tray 38 therein. Which tray 38 is shown as including pivoting handles 48 that are secured to opposite ends and are for gripping for lifting the tray out from the primary chamber 35.

Medical instrument sterilization takes place in the primary chamber 35 that is arranged to be removable from the secondary chamber 18 for transport in a sealed state to an operating room. Accordingly, both a sterilizing agent inlet line 50 and an exhaust line 51, as shown in the FIGS., are connected into the primary chamber pan 36 by quick release couplings 52 and 53, respectively. Which quick release couplings may be standard pneumatic hose type couplings where a male member that is secured to the end of the inlet or exhaust lines 50 or 51 is fitted into a female member secured across an opening into the pan 36. Which female member includes a spring loaded collar that is arrangement for movement away from the male member, against its spring biasing, to release a ball that is thereby allowed to pass into a groove formed around which male member. With release of the female member collar the spring biasing returns the collar to its original attitude where the ball is prohibited from rolling out of the male member groove, locking the male and female members together. In practice, when the male member is released out of the female member, as set out above, the opening through the female member is automatically closed. As shown best in FIG. 5, the quick release coupling 52 female member attaches to the primary chamber 35. The nozzle end provides a speeding up of a flow of sterilization agent into the primary chamber 35, creating turbulence in that flow that is circulated throughout the chamber scouring, cleaning and sterilizing medical instruments therein.

Figure 5:
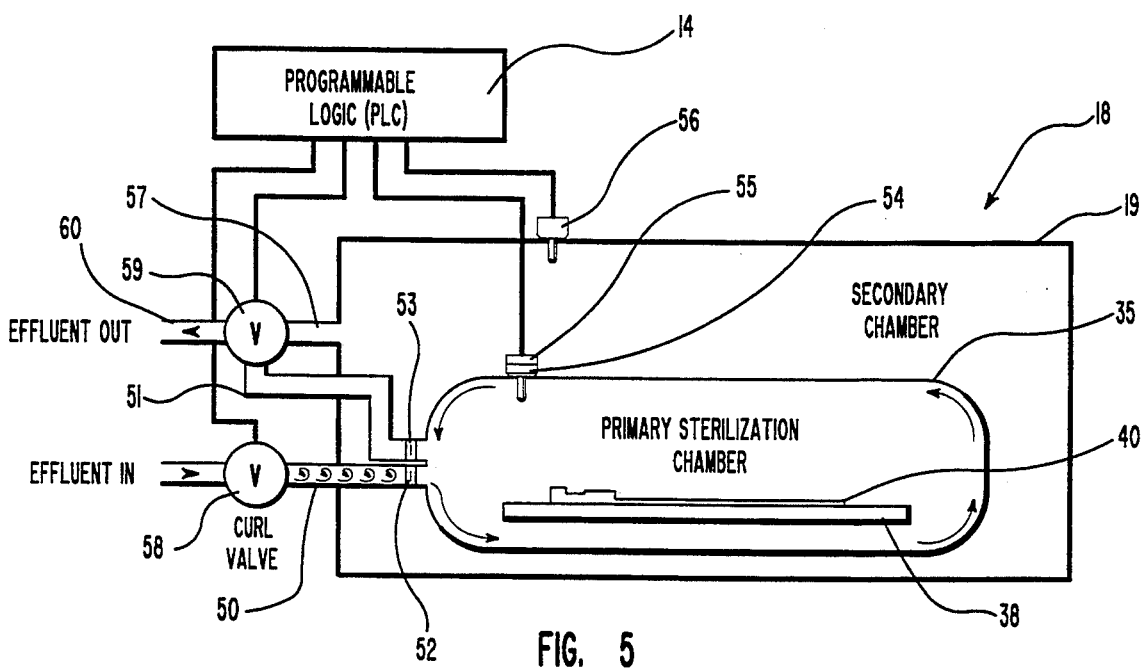
FIG. 5 is a side elevation schematic of the secondary safety chamber containing the primary sterilization chamber and showing sensors and gas valves operated by a programmable logic circuit.

Humidity probes or sensors 54 and 56, respectively, are preferably provided for sensing humidified sterilization agent presence in the primary and secondary chambers, 35 and 18, respectively, by sensing humidity in which chambers. Within the scope of this disclosure the humidity probes or sensors 54 and 56 can be physically mounted in the primary and secondary chambers, 35 and 18, respectively, as shown best in FIG. 5, or can be arranged in the primary chamber exhaust line 51 and a secondary chamber exhaust line 57, as shown best in FIG. 3. Shown best in FIG. 4, the secondary chamber 18 exhaust line 57 end 57a is mounted into the secondary chamber back wall 22 wherethrough the primary chamber inlet and exhaust lines 50 and 51 are fitted and sealed. Both of which exhaust lines 51 and 57 connect into an effluent out line 60, as shown in FIGS. 3 and 5. Where the primary chamber 35 humidity probe or sensor 54 is for mounting into the pan 36, as shown in FIG. 5, it includes a base that extends beyond the pan surface. Which base is preferably a female electrical plug that is arranged for receiving and electrically coupling to a male electrical coupling 55 that is connected by wire, as is the secondary chamber humidity probe or sensor 56, into the programmable logic circuit (PLC) 14. Chamber humidity readings are thereby provided to the PLC 14 that are utilized for controlling the sterilization cycle and chamber venting. The quick disconnect inlet and exhaust line couplings 52 and 53, respectively, and the humidity probe or sensor 54 and male coupling 55, facilitate the removal of the primary chamber 35 from the secondary chamber 18 after sterilization. The primary chamber 35 containing sterilized medical instruments can then be transported, in a sealed state, to an operating room for opening by medical personnel. The primary chamber 35 is therefore preferably both a sterilization vessel and transport container. For these duel roles, the primary chamber pan 36, lid 37 and tray 38 are preferably formed from an appropriate ridged material, such as stainless steel, that is not effected by the preferred sterilization agent humidified ozone, and is convenient to carry, utilizing handles 42, to an operating room.

Hereinabove has been set out a description of a primary sterilization and transport chamber 35 and secondary safety chamber 18 of a sterilization system that the present invention is suitable for inclusion with for performing a sterilization cycle carried on in which primary sterilization chamber. As set out, the sterilization cycle is automated under the control of the programmable logic circuit (PLC) 14 with an operator inputting information at control panel 13 buttons, with system functions shown at display 16. On starting the sterilization cycle the PLC 14 opens valve 58, as illustrated in FIG. 5, that is identified as effluent in, passing and circulating humidified ozone to within the primary chamber 35. At the conclusion of which sterilization cycle, the PLC 14 operates an effluent out, valve 59 to vent both the primary and secondary chambers 35 and 18 through their respective exhaust lines 51 and 57. For convenience, the respective exhaust lines 51 and 57 along with a system vent line 90 are shown combined into an effluent out line 60 as shown in FIG. 3, but in practice they are preferably separate lines shown as 70a, 70b and 70c in FIG. 6, as discussed below. In operation, the respective primary and secondary chamber humidity probes or sensors 54 and 56 must sense an absence of the humidified sterilization agent in both of the chambers before the PLC 14 will release the actuator 30, allowing for opening of the secondary chamber lid 24, for removal of the primary chamber 35.

Figure 3:
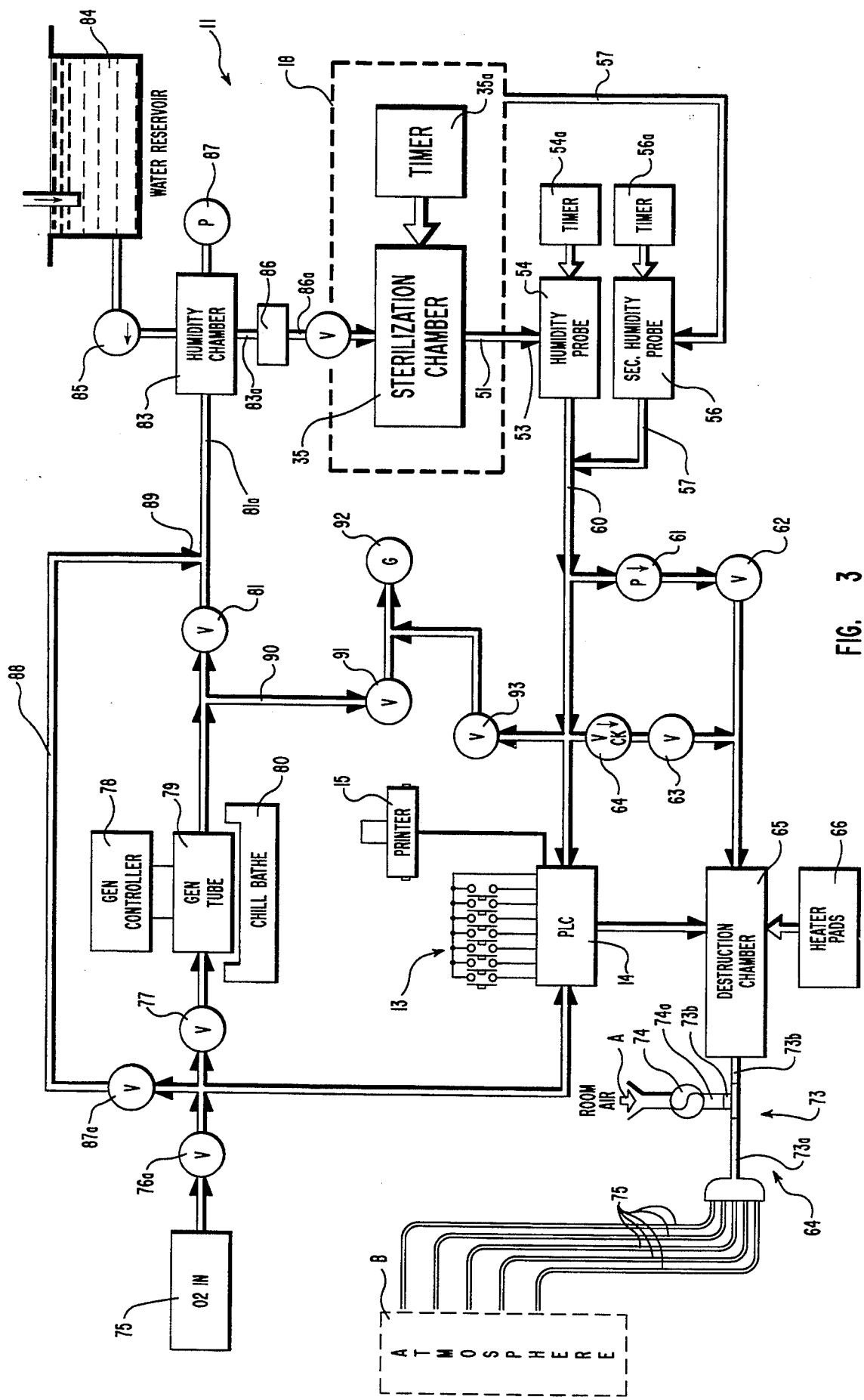
FIG. 3 is a block flow schematic of the ozone sterilization system of FIGS. 1 and 2, showing the invention in blocks with a single line shown for transferring the spent sterilization agent thereto that should be taken as individual lines from the primary sterilization chamber, the secondary safety chamber and system vent lines.

In the effluent venting process, as illustrated by the block flow schematic of FIG. 3, effluent from the primary and secondary chambers 35 and 18 is pulled through the effluent out line 60 by pump 61, that flow passing through valve 62 and into the spent sterilization agent destruct and ambient air mixing device 64 of the invention, earlier referred to herein as destruct device. Additionally, for controlling effluent passage for destruction, the effluent out line 60 connects to the PLC 14 for provide a sensing of effluent presence, and is joined to an ozone emergency venting line 90. Which line 90 extends from an ozone generation tube 79 that connects through valves 91 and 93 and contacts an in line pressure gauge 92 that provides data to the PLC 14. The junction of the effluent out line 60 with the ozone emergency venting line 90 connects through a check valve 63a and valve 63 to vent ozone and humidified ozone into the destruct device 64.

Figure 6:
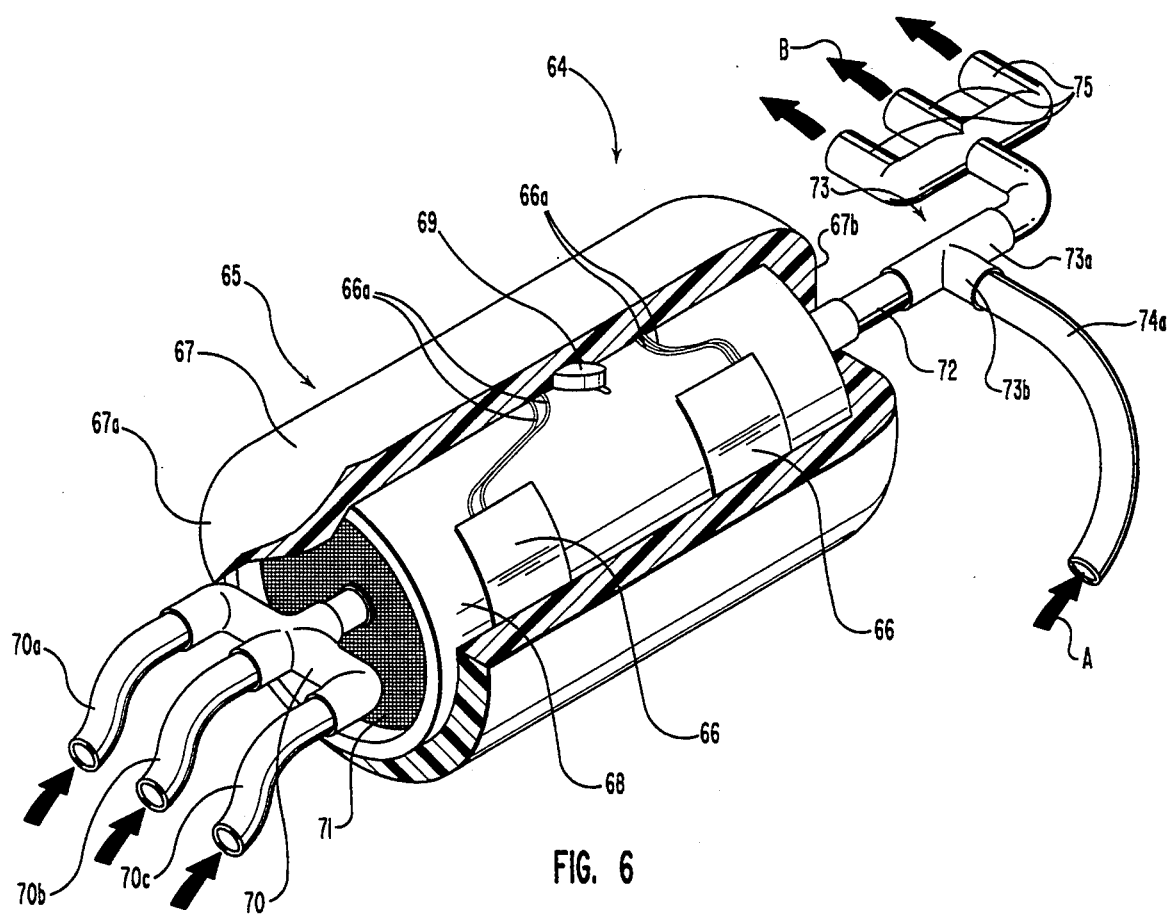
FIG. 6 is a profile perspective view taken from one end of the spent sterilization agent destruct and ambient air mixing device of the invention shown removed from the ozone sterilization system.

The destruct device 64, of the invention, shown in FIG. 3 and in detail in FIG. 6, includes a destruction chamber 65 that contains heater pads 66. The destruction chamber 65, as shown best in FIG. 6, has a closed insulative outer body 67, shown as a cylinder though another appropriate shape of container could be so used. The outer body is preferably formed from an insulative material and is closed at both ends. Within the insulative outer body 67 is contained an inner body 68 that is preferably formed as a cylinder from a conductive material, such as metal, and whereon the heater pads 66 are shown attached. The heater pads are connected by wires 66a to a source of electricity, and a thermostat sense/switch 69 is mounted onto which inner body 68 for sensing the temperature thereof and is linked to the source of electricity for switching on and turning off a flow of electricity to the heater pads 66 for closely controlling the temperature of the inner body 68 to provide a total and complete reduction of ozone $O_3$ to oxygen $O_2$ that is passing through the inner body.

Spent sterilization agent or effluent is directed through the outer body 67 end 67a into the inner body 68 of the destruction chamber 65 through a T coupling 70 that connects to lines 70a, 70b, and 70c from the primary sterilization and secondary safety chambers and system vent line. The sterilization agent or effluent entering the inner body 68 is circulated through a mesh core that is a catalytic converter 71 that along with the controlled heat provided by the heater pads 66, provides for a full and complete reduction of the sterilization agent to an inert state where all the ozone $O_3$ in the mixture is reduced to oxygen $O_2$. In practice the mesh material utilized in catalytic converter is one that provides for a reduction of ozone $O_3$ to oxygen $O_2$, and a number of materials are suitable for use as the catalytic converter 77, which mesh is rolled into a cylinder and fitted into the inner body 68. The combination of the heating of the inner body 68 and contained catalytic converter to a set temperature completely reduces the ozone $O_3$ of the sterilization agent passing therethrough to oxygen $O_2$ that is then vented to atmosphere.

After passage through the catalytic converter 71, the inert sterilization agent is vented from the outer body 67 end 67b into a vent and ambient air inflow line 72, hereinafter referred to as vent line. The vent line 72 connects to a through leg 73a of a T coupling 73 that includes an intersecting leg 73b whereto is fitted an fan blower line 74a. The fan blower line 74a receives an air flow from a fan blower 74, shown best in FIG. 3, that pulls in a fresh air flow, illustrated as arrow A, from the ambient air surrounding the sterilization chamber. The entering air mixes with the inert spent sterilization agent and is vented from the T coupling through leg 73a into a plurality of exhaust lines 75 that vent to atmosphere, illustrated as arrow B in FIG. 6 and as a broken line box in FIG. 3. With the inclusion of the destruct device 64 of the invention in a sterilization system 11 the destruct device provides for safely rendering inert all spent sterilization agent as is purged from the primary sterilization chamber 35, the secondary safety chamber 18 and vent line 90. Which sterilization agent or effluent, as set out above, is preferably a humidified ozone mixture.

For producing the humidified ozone gas flow that is the sterilization agent or effluent, as illustrated in FIG. 3, oxygen, shown as block 75, is passed through an oxygen inlet valve 76a and ozone generation valve 77 into a generation tube 79. As shown, the generation tube 79 is controlled by a generation controller 78 and is maintained within a chill bathe 80 for maintaining the produced ozone at or near atmospheric pressure and room or standard temperature conditions. On opening of valve 81, ozone from generation tube 79 passes through line 81a to a humidity chamber 83. A water reservoir 84 is provided for supplying water, under pressure, from a pump 85, to the humidity chamber 83.

A temperature control 86 is provided for maintaining a desired temperature of ozone $O_3$ and water vapor in humidity chamber 83. Which temperature, in practice is preferably approximately thirty one (31) degrees Celsius (C), for maintaining a desired ozone $O_3$ concentration of approximately twelve (12) percent ozone, to ten (10) water, plus or minus three (3) percent, to oxygen $O_2$, that may be produced by spraying water under pressure through a nozzle producing a fine spray in which humidity chamber 83, or by other appropriate humidification procedure, within the scope of this disclosure. The humidified ozone $O_3$ is passed from humidity chamber 83 through line 50 shown in FIG. 5 into the primary sterilization chamber 35, as set out hereinabove. Which humidified ozone $O_3$ is preferably at or near atmospheric pressure and room or standard temperature. This greatly simplifies sterilization operations as the primary chamber 35 is required only to contain low temperature and pressure of gas, simplifying the sealing requirements of both the primary and secondary chambers 35 and 18, respectively.

For start-up, and for controlling ozone $O_3$ concentrations during operations, valve 87a may be opened for routing oxygen $O_2$ around the ozone generation tube 79. With valve 87a open, oxygen $O_2$ passes through line 88 to junction 89 with line 81a, passing oxygen $O_2$ to the humidity chamber 83. Oxygen $O_2$ may therefore also be conveniently utilized for providing system purging after suspension of ozone $O_3$ generation. In the event of a termination of the sterilization cycle prior to completion it is, of course, necessary to remove the ozone sterilization agent from the system. This is accomplished by shutting down the ozone generation tube 79 and closing valve 81. In which shut down state oxygen $O_2$ is preferably routed, as set out above, to the humidity chamber 83. The ozone generator is thereby bypassed, to purge the sterilization chamber 35. For venting ozone as is present in the generation tube 79 and connecting lines, through vent line 90, a valve 91 is opened and ozone presence in the generation tube and lines is monitored by pressure gauge 92. Opening of valve 93 allows for continued effluent passage in vent line 90 to both the PLC 14, for monitoring and control, and through the check valve 63a and valve 63 for destruction in the destruct device 64 of the invention, as set out above.

Timers 54a and 56a are provided for monitoring component operations during a sterilization cycle that are connected, respectively, to the humidity probe 54, that senses humidified ozone $O_3$ presence in the sterilization chamber 35, and to secondary humidity probe 56, that monitors humidified ozone $O_3$ presence in the secondary chamber 18. The timers 54a and 56a are started when the humidity probes indicate an absence of humidified ozone $O_3$, for continuing the system purging for a period of time to insure a full evacuation of humidified ozone $O_3$ from the primary and secondary chambers prior to system opening. Further, a timer 35a is provided that is set by an operator to a time period of the sterilization cycle for the particular medical instruments to be sterilized. Which primary sterilizer chamber timer 35a is programed and that setting is passed to the PLC 14 for setting the periods for system component functioning.

While a preferred form and embodiment of my invention in a sterilization system spent sterilization agent destruct and ambient air mixing device and its functioning within an ozone sterilization system has been shown and described herein it should be understood that the present disclosure is made by way of example only, and that variations and changes can be made thereto without departing from the subject matter coming with the scope of the following claims, and a reasonable equivalency thereof, which claims should be regarded as my invention.

I claim:

1. A spent sterilization agent destruct and ambient air mixing device in combination with a medical instrument sterilizer with an ozone generator comprising, a closed outer housing, arranged as a component of a medical instrument sterilizer with an ozone generator; an inner body for fitting in said closed outer housing that is open therethrough; means for passing a flow of a spent ozone $O_3$ sterilization agent into one end of said inner body; a catalytic converter means for fitting within said inner body that receives the flow of spent ozone $O_3$ sterilization agent and converts ozone $O_3$ in said flow into oxygen $O_2$ rendering said spent ozone $O_3$ sterilization agent flow inert; electrically operated heater pad means mounted to the inner body for providing a controlled heating of the spent effluent flow through the catalytic converter means to increase the efficiency of the reactive process taking place within said catalytic converter means; and fan means connected for passing ambient air into a flow from a discharge end of said inner body for mixing with said inert spent sterilization agent containing oxygen $O_2$ as has passed through said inner body and for venting said mix of ambient air and inert spent sterilization flow to atmosphere.

2. A spent sterilization agent destruct and ambient air mixing device as recited in claim 1, wherein the closed outer housing is formed from an insulative material into a cylindrical shape; and the inner body is formed as a cylinder from a conductive material that is open at both ends and receives said catalytic converter means fitted therein.

3. A spent sterilization agent destruct and ambient air mixing device as recited in claim 1, wherein the means for passing the flow of spent ozone $O_3$ sterilization agent into the inner body is a vent line that is fitted through the closed outer housing end and extends from an end of a vertical leg of a T coupling, with a horizontal or cross leg of said T coupling connecting to receive 4. A spent sterilization agent destruct and ambient air mixing device as recited in claim 1, further including sensor means arranged within the closed outer housing for measuring temperature within said catalytic converter means and for controlling passage of electrical current to the electrically operated heater pad means for controlling heat output to within set limits. a spent effluent flow from a primary sterilization chamber vent line, a secondary safety chamber vent line, and a vent line.

5. A spent sterilization agent destruct and ambient air mixing device as recited in claim 1, wherein the fan means further connects to a plurality of vent lines for venting the inert spent sterilization agent to atmosphere.

* * * * *

UNITED STATES PATENT AND TRADEMARK OFFICE
CERTIFICATE OF CORRECTION

PATENT NO. : 5,334,355
DATED : Aug. 2, 1994
INVENTOR(S) : Chris G. Faddis

It is certified that error appears in the above-identified patent and that said Letters Patent is hereby corrected as shown below:

In Claim 3, line 7, found at Column 10, line 49, after "receive" add --a spent effluent flow from a primary sterilization chamber vent line, a secondary safety chamber vent line, and a vent line.--

In Claim 4, line 7, found at Column 10, line 56, after "limits." delete "a spent effluent flow from a primary sterilization chamber vent line, a secondary safety chamber vent line, and a vent line."

Signed and Sealed this

Twenty-ninth Day of August, 1995

Attest:

BRUCE LEHMAN

Attesting Officer     Commissioner of Patents and Trademarks